(12) United States Patent
Pospisilik et al.

(10) Patent No.: US 7,491,848 B2
(45) Date of Patent: Feb. 17, 2009

(54) PROCESS FOR MAKING DESVENLAFAXINE

(75) Inventors: Karel Pospisilik, Krtiny (CZ); Lambertus Thijs, Wijchen (NL)

(73) Assignee: Synthon IP Inc., Gainesville, VA (US)

( * ) Notice: Subject to any disclaimer, the term of this patent is extended or adjusted under 35 U.S.C. 154(b) by 16 days.

(21) Appl. No.: 11/643,298

(22) Filed: Dec. 20, 2006

(65) Prior Publication Data

US 2007/0299283 A1    Dec. 27, 2007

Related U.S. Application Data

(60) Provisional application No. 60/752,098, filed on Dec. 20, 2005.

(51) Int. Cl.
*C07C 213/00*    (2006.01)

(52) U.S. Cl. ............................... 564/336

(58) Field of Classification Search ............... None
See application file for complete search history.

(56) References Cited

U.S. PATENT DOCUMENTS 4,535,186 A    8/1985   Husbands et al.
5,043,466 A    8/1991   Shepard

FOREIGN PATENT DOCUMENTS

| | | |
|---|---|---|
| EP | 112669 | 7/1983 |
| WO | WO 00/32555 | 6/2000 |
| WO | WO 00/32556 | 6/2000 |
| WO | WO 00/59851 | 10/2000 |
| WO | WO 03/48104 | 4/2001 |
| WO | WO 02/64543 | 8/2002 |

*Primary Examiner*—Samuel A Barts
(74) *Attorney, Agent, or Firm*—Mark R. Buscher

(57) ABSTRACT

Desvenlafaxine is formed from venlafaxine by the use of a demethylating agent comprising a metal sulfide, such as sodium sulfide, and optionally selenium.

30 Claims, No Drawings

PROCESS FOR MAKING DESVENLAFAXINE

This application claims the benefit of priority under 35 U.S.C. § 119(e) from prior U.S. provisional patent application Ser. No. 60/752,098, filed Dec. 20, 2005, the entire contents of which are incorporated herein by reference.

BACKGROUND OF THE INVENTION

The present invention relates to a process for making desvenlafaxine. Desvenlafaxine, chemically 1-[2-(Dimethylamino)-1-(4-hydroxyphenyl)ethyl]-cyclohexanol of the formula (1):

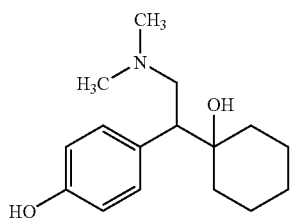

is an active metabolite of the known pharmaceutical agent venlafaxine, the compound of formula (2).

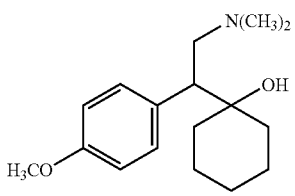

As is seen from the above, desvenlafaxine differs from venlafaxine in that the former is missing a methyl group in the phenolic substituent; e.g. is "des-methyl" hence 'desvenlafaxine.' The molecule of the formula (1) has one center of optical activity. The desvenlafaxine as used herein comprises the racemic form, the single enantiomer, and mixtures of enantiomers. Desvenlafaxine is being tested as an improved form of venlafaxine and may one day replace venlafaxine in medical treatments. Accordingly, several patents are already known concerning desvenlafaxine.

For example, desvenlafaxine was disclosed in the patent EP 112669/U.S. Pat. No. 4,535,186 owned by American Home Products. Furthermore, it has been disclosed in the patent application WO 00/59851 of Sepracor. More recently, WO 02/64543 discloses that an advantageous salt form of desvenlafaxine is a (1:1) succinate salt and that the crystalline product is a monohydrate.

Various processes are also known for making desvenlafaxine. Many of these processes start from venlafaxine and convert it to desvenlafaxine via, in essence, a demethylation of venlafaxine. Such a process has been generically suggested in U.S. Pat. No. 5,043,466.

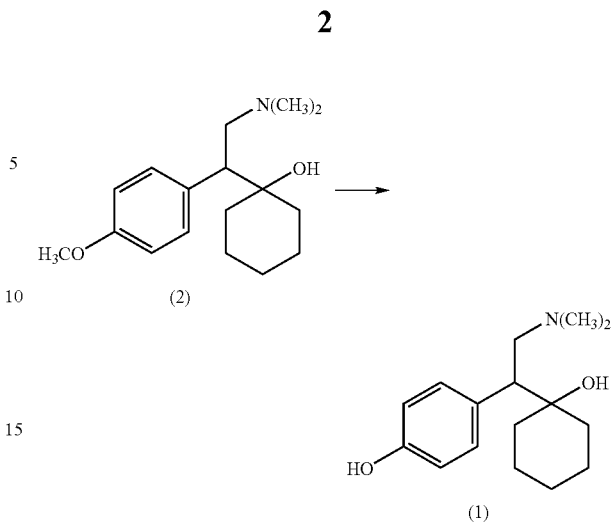

However, in general, the substituted phenoxy group is a very stable moiety against nucleophilic substitution and thus the demethylation reaction requires special reagents and drastic conditions. Furthermore, the reagent should not attack the tertiary hydroxy group in the molecule.

WO 00/59851, WO 00/32556 and WO 00/32555 disclose a process for producing desvenlafaxine starting from venlafaxine using lithium diphenylphosphide (made in situ from diphenyl phosphine and n-butyllithium) as the demethylation agent and tetrahydrofuran (THF) as a solvent. A disadvantage of this process is that the concentration of the material in the solvent is very low. Apparently the demethylation of venlafaxine is complicated by the formation of a largely insoluble lithium salt of venlafaxine that is formed in the THF solvent.

WO 02/64543 discloses that an alkali metal salt of a trialkyl borohydride (e.g. L-selectride) at a temperature from 60 to 140° C. may be used for demethylation. The formed alkali metal salt of the desvenlafaxine is converted to the free base of desvenlafaxine by a neutralization with an acid. The process is relatively expensive due to the cost of the reagents.

WO 03/48104 discloses a process of demethylation employing a dodecane thiol (or benzenethiol) in the presence of sodium methanolate in methanol as the demethylation agent, polyethyleneglycol 400 as the solvent, reaction temperature of 180-200° C. and a reaction time of 2-5 hours. After neutralization of the reaction product to pH approx. 9.5 in the presence of isopropanol, the free base of desvenlafaxine is obtained. Polyethylene glycol can be disadvantageous as it is difficult to be recycled after use and the overall process suffers from the need for high reaction temperatures.

Therefore, it would be desirable to find an alternative and preferably economically efficient process for demethylation of venlafaxine.

SUMMARY OF THE INVENTION

The present invention relates to the discovery of a new process for converting venlafaxine into desvenlafaxine via demethylation. Accordingly, a first aspect of the invention relates to a process that comprises combining in a solvent a metal sulfide compound, venlafaxine, and optionally selenium; and heating said combination sufficiently to form desvenlafaxine.

Another aspect of the invention relates to a process that comprises demethylating venlafaxine with a demethylation agent in a solvent to form desvenlafaxine, wherein the demethylation agent comprises a metal sulfide compound and optionally selenium.

In both aspects, selenium is preferably additionally present. The solvent is typically a dipolar aprotic solvent such as sulfolane (also known as tetramethylene sulfone (tetrahydrothiophene-1,1-dioxide), dimethylsulfoxide, hexamethylphosphoric acid triamide, N-methyl-ε-caprolactam, and, preferably, 1-methyl-pyrrolidone (sometimes also referred to in the chemical arts as 1-methyl-2-pyrrolidinone).

DETAILED DESCRIPTION OF THE INVENTION

The present invention is based on the discovery that metal sulfide compounds can be useful demethylating agents for converting venlafaxine to desvenlafaxine. As used herein a "metal sulfide compound" means a compound formed of one or more divalent sulfur atoms and at least one alkali metal or alkaline earth metal. Generally the metal is sodium, potassium, calcium or magnesium. Typically only one sulfur atom is present, e.g. a binary compound of divalent sulfur and a metal, but for purposes of the present application poly-sulfurs are also included. Examples of metal sulfide compounds include sodium sulfide ($Na_2S$), potassium sulfide, calcium sulfide, magnesium sulfide, and potassium polysulfide. In general, sodium sulfide is preferred due to its relative low cost and ease in acquiring. The invention will be further described with reference to sodium sulfide for ease of illustration.

Sodium sulfide ($Na_2S$) is commercially available as an anhydrate and also as a hydrated form. The hydrated sodium sulfide is substantially cheaper than the anhydrous compound and can be used, but it is generally desired that the bound crystalline water be removed therefrom prior to the reaction with venlafaxine. Any process may be applied including vacuum drying and/or azeotropic removal in a suitable solvent, e.g. in toluene. Further, a convenient way comprises heating the hydrated sulfide in the solvent that shall be used for the demethylation reaction to a temperature of about 140° C., whereby the water is distilled off. This can allow for essentially an in situ formation of the water-free sodium sulfide, even after addition/combining with venlafaxine.

The starting venlafaxine may be obtained by various procedures known in the art. It may be used in the process of our invention preferably in its isolated form, but this is not strictly required.

The solvent is any relatively inert reaction medium in which the venlafaxine and sodium sulfide are soluble, at least to some extent. Selecting a preferred solvent for the demethylation reaction is complicated by low solubility of the sodium sulfide and the possibility of ion-pair association of the sulfide anion. Protic solvents including water should normally be avoided; aprotic solvents are generally used. A suitable solvent is preferably a dipolar aprotic solvent with a sufficiently high boiling point, such as sulfolane, dimethylsulfoxide, hexamethylphosphoric acid triamide, N-methyl-ε-caprolactam, and 1-methylpyrrolidone. Advantageously the solvent is distillable without decomposition to allow a simple regeneration of the solvent after the reaction. Therefore, polymeric liquids such as polyethylene glycol may be avoided, if desired. The above specified solvents are also distillable. The typical solvent is 1-methylpyrrolidone.

The reaction proceeds by heating the venlafaxine and sodium sulfide (preferably 2 to 6 moles of sodium sulfide are provided per mole of venlafaxine) in the solvent at a sufficient temperature, generally from about 130 to 160° C., more typically 140-150° C. The sodium sulfide may be added at once or may be added in portions. Conversely, the venlafaxine can be added to the sodium sulfide in one or more portions. It should be understood that "heating" includes maintaining an elevated temperature such as 140° C. and is not meant to imply or otherwise require that the venlafaxine and sodium sulfide are combined at lower temperatures; though of course such is also included. For example, "heating" may simply be maintaining the temperature of the sodium sulfide after distilling off the crystalline bound water therefrom and/or while adding the venlafaxine thereto. In short, the heating and combining of the venlafaxine and demethylating agent can be carried out sequentially (in either order), simultaneously, or in overlapping fashion (e.g. a partial addition followed by heating and then further addition). The course of the reaction may be monitored by a suitable method, e.g. by HPLC, if desired. Typically the reaction is carried out for at least several hours and often for 4 to 50 hours. Usually the reaction is continued until substantially complete.

In an advantageous mode, the speed of the reaction may be increased by adding an essentially equimolar amount of selenium, based on the amount of metal sulfide compound, to the reaction mixture. The nucleophilic cleavage of the venlafaxine is probably caused or aided by sodium selenide which is likely formed in-situ and is more nucleophilic than the sulfide. In this regard, a "demethylation agent" as used herein refers to the reagent(s) that is added to the solvent regardless of any subsequent in situ conversions. Thus, the combination of sodium sulfide and selenium is a preferred demethylating agent or system, even though selenium sulfide is likely actually reacting; i.e. actually demethylating. Also it should be understood that single and multiple reagents are contemplated by the singular "demethylating agent." Thus the demethylating agent can comprises a sodium sulfide and potassium sulfide, or the preferred combination of sodium sulfide and selenium.

The reaction generally proceeds under an atmosphere of inert gas, e.g. nitrogen.

At or after the termination or completion of the reaction, the reaction mixture is advantageously treated with water. The addition of water converts the sodium salt of desvenlafaxine, which is the primary product formed from the demethylation reaction with sodium sulfide, to desvenlafaxine base and facilitates isolation in solid state of desvenlafaxine. Surprisingly, the addition of water allows the present invention to avoid the use of acid to neutralize the reaction mixture. In the case of 1-methylpyrrolidone as a solvent, the desvenlafaxine base, especially if formed via water addition as described above, crystallizes quite easily after cooling the reaction mixture and adding some low polar liquid as a contrasolvent, e.g. ethyl acetate. The rest of the unreacted sulfide reagent and the side products generally remain dissolved in the solvent medium.

As mentioned above, the sodium sulfide in the preceding description can be replaced by any metal sulfide compound. While operable, some other sulfides may not work as efficiently. For example, potassium polysulfide generally works more slowly than sodium sulfide.

While the inventive process for making desvenlafaxine has been disclosed and exemplified on the case of racemic product, it is understood that it may be used without limitation also for making single enantiomers of desvenlafaxine, should the corresponding single enantiomer of venlafaxine be used as the starting material.

EXAMPLE 1

A mixture of 5.7 g of sodium sulfide hydrate, and 6 mL of 1-methylpyrrolidone was heated to 145° C. under nitrogen, and then 3.5 g of venlafaxine dissolved in 6 mL of 1-methylpyrrolidone was added. The mixture was stirred and heated at 145° C. under nitrogen, approx. 3.5 g of liquid was distilled off. Reaction mixture was heated at 145° C. for 30 hours, then it was cooled and mixed with 70 mL of ethylacetate and 50 mL of water. The mixture was placed into a refrigerator and after 2 hours crystals were filtered and dried to give 2.5 g of desvenlafaxine.

Yield 75%.

EXAMPLE 2

A mixture of 1.90 g of anhydrous sodium sulfide, 2.0 g of selenium and 6 mL of 1-methylpyrrolidone was heated to 145° C. under nitrogen, and then 3.5 g of venlafaxine dissolved in 10 mL of 1-methylpyrrolidone was added. The mixture was stirred and heated at 145° C. under nitrogen. Reaction mixture was heated at 145° C. for 16 hours, then it was cooled and mixed with 70 mL of ethylacetate and 50 mL of water. The mixture was placed into a refrigerator and crystals were filtered. After being recrystallized from 45 mL of ethanol, 2.0 g of desvenlafaxine was obtained with the yield 60%.

EXAMPLE 3

A mixture of 78.5 g of anhydrous sodium sulfide, and 525 mL of 1-methylpyrrolidone was heated to 145° C. under nitrogen, and then 145 g of venlafaxine was added. The mixture was stirred and heated at 145° C. under nitrogen for 30 hours, then it was cooled and mixed with 2.9 L of ethylacetate and 2.0 L of water. The mixture was kept in the refrigerator overnight, crystals were filtered and dried to give 106.5 g of desvenlafaxine. Yield 77%.

The entire disclosure in each of the above-mentioned patents and patent applications is incorporated herein by reference. The invention having been described, it will be readily apparent to those skilled in the art that further changes and modifications in actual implementation of the concepts and embodiments described herein can easily be made or may be learned by practice of the invention, without departing from the spirit and scope of the invention as defined by the following claims.

We claim:

1. A process, which comprises combining in a solvent a metal sulfide compound, venlafaxine, and optionally selenium; and heating said combination sufficiently to form desvenlafaxine, wherein said metal sulfide compound is selected from sodium sulfide, potassium polysulfide, calcium sulfide, magnesium sulfide, and potassium sulfide.

2. The process according to claim 1, wherein said metal sulfide compound is sodium sulfide or potassium polysulfide.

3. The process according to claim 2, wherein said metal sulfide compound is sodium sulfide.

4. The process according to claim 1, wherein selenium is combine in said solvent.

5. The process according to claim 4, wherein said selenium is combined in an approximately equimolar amount with said metal sulfide.

6. The process according to claim 3, wherein said selenium is combined in said solvent.

7. The process according to claim 1, wherein said solvent is a dipolar aprotic solvent.

8. The process according to claim 7, wherein said solvent is 1-methylpyrrolidone.

9. The process according to claim 2, wherein said heating achieves a temperature within the range of 130° C - 160° C.

10. The process according to claim 9, wherein said temperature is within the range of 140° C- 150° C.

11. The process according to claim 1, which comprises adding said venlafaxine to the heated solvent containing said metal sulfide and selenium to thereby form said desvenlafaxine.

12. The process according to claim 1, wherein said combining and heating are carried out under an inert atmosphere.

13. The process according to claim 12, wherein said atmosphere is nitrogen.

14. The process according to claim 1, which further comprises isolating said desvenlafaxine in a solid state from a remaining reaction mixture.

15. The process according to claim 14, wherein the isolation comprises adding water and a low polar liquid to the remaining reaction mixture and cooling to precipitate said desvenlafaxine.

16. The process according to claim 15, wherein said low polar liquid is ethyl acetate.

17. The process according to claim 1, wherein said metal sulfide is sodium sulfide, selenium is combined in said combination, said solvent is 1-methylpyrrolidone, and said heating and combining are carried out under nitrogen atmosphere.

18. A process for demethylating venlafaxine with a demethylation agent in a solvent to form desvenlafaxine, the improvement for which comprises a metal sulfide compound and optionally selenium as said demethylation agent, wherein said metal sulfide compound is selected from sodium sulfide, potassium polysulfide, calcium sulfide, magnesium sulfide, and potassium sulfide.

19. The process according to claim 18, wherein said demethylating agent is sodium sulfide and selenium.

20. The process according to claim 19, wherein said solvent is 1-methylpyrrolidone.

21. A process, which comprises combining in a solvent a metal sulfide compound, venlafaxine, and selenium; and heating said combination sufficiently to form desvenlafaxine.

22. The process according to claim 21, wherein selenium is combined in said solvent in an approximately equimolar amount with said metal sulfide.

23. The process according to claim 21, wherein said solvent is a dipolar aprotic solvent.

24. The process according to claim 23, wherein said solvent is 1-methylpyrrolidone.

25. The process according to claim 21, which comprises adding said venlafaxine to the heated solvent containing said metal sulfide and selenium to thereby form said desvenlafaxine.

26. The process according to claim 21, wherein said combining and heating are carried out under an inert atmosphere.

27. The process according to claim 26, wherein said atmosphere is nitrogen.

28. The process according to claim 21, which further comprises isolating said desvenlafaxine in a solid state from a remaining reaction mixture.

29. The process according to claim 28, wherein the isolation comprises adding water and a low polar liquid to the remaining reaction mixture and cooling to precipitate said desvenlafaxine.

30. The process according to claim 29, wherein said low polar liquid is ethyl acetate.

* * * * *